United States Patent [19]

Patil et al.

[11] 4,299,501
[45] Nov. 10, 1981

[54] CONTINUOUS PROCESS FOR THE PREPARATION OF SEMISOLID DISPERSIONS

[75] Inventors: Deepak R. Patil, Livingston; Glenn A. VanBuskirk, Bernardsville, both of N.J.

[73] Assignee: Ortho Pharmaceutical Corporation, Raritan, N.J.

[21] Appl. No.: 65,665

[22] Filed: Aug. 10, 1979

[51] Int. Cl.³ .................... B01F 13/00; B01F 15/02; B01F 15/06
[52] U.S. Cl. .................................. 366/349; 366/136; 366/144; 366/159
[58] Field of Search ................. 366/349, 341, 22, 23, 366/24, 76, 91, 96, 136, 159, 144, 145, 149, 336

[56] References Cited

U.S. PATENT DOCUMENTS

| 1,792,067 | 2/1931 | Brown | 366/76 |
| 2,389,012 | 11/1945 | Trist | 366/136 |
| 3,572,649 | 3/1971 | Joel | 366/136 |
| 3,784,169 | 1/1974 | Bockmann | 366/159 |

Primary Examiner—Edward J. McCarthy
Attorney, Agent, or Firm—Benjamin F. Lambert

[57] ABSTRACT

A semicontinuous or continuous process for preparing semisolid dispersions is provided wherein oil and water phases are circulated from a single vessel through a system of mixers and homogenizers until a dispersion is obtained.

4 Claims, 3 Drawing Figures

CONTINUOUS PROCESS FOR THE PREPARATION OF SEMISOLID DISPERSIONS

The present invention relates to a method for the preparation of semisolid dispersions.

The general procedure for preparing semisolid dispersions, i.e. creams, jellies, ointments and the like, consists of a three-step batch operation wherein a hot oil phase and a hot aqueous phase are brought together, thoroughly mixed to cause the two phases to form a substantially homogeneous mixture and then cooled until the homogeneous mixture congeals and forms a cream.

This procedure has been generally accepted throughout the pharmaceutical industry for preparing cream bases in spite of the fact that it entails three separate operations. In addition, restricted production time and extensive material handling are additional drawbacks attendant to these operations.

In accordance with the present invention, a process for preparing semisolid dispersions is provided which can be carried out continuously and which is substantially more efficient than the prior art method.

The process of the present invention comprises combining the two immiscible phases in one vessel and circulating the mixture through a system of mixers and/or homogenizers until the desired homogeneity is achieved.

Figure 1:
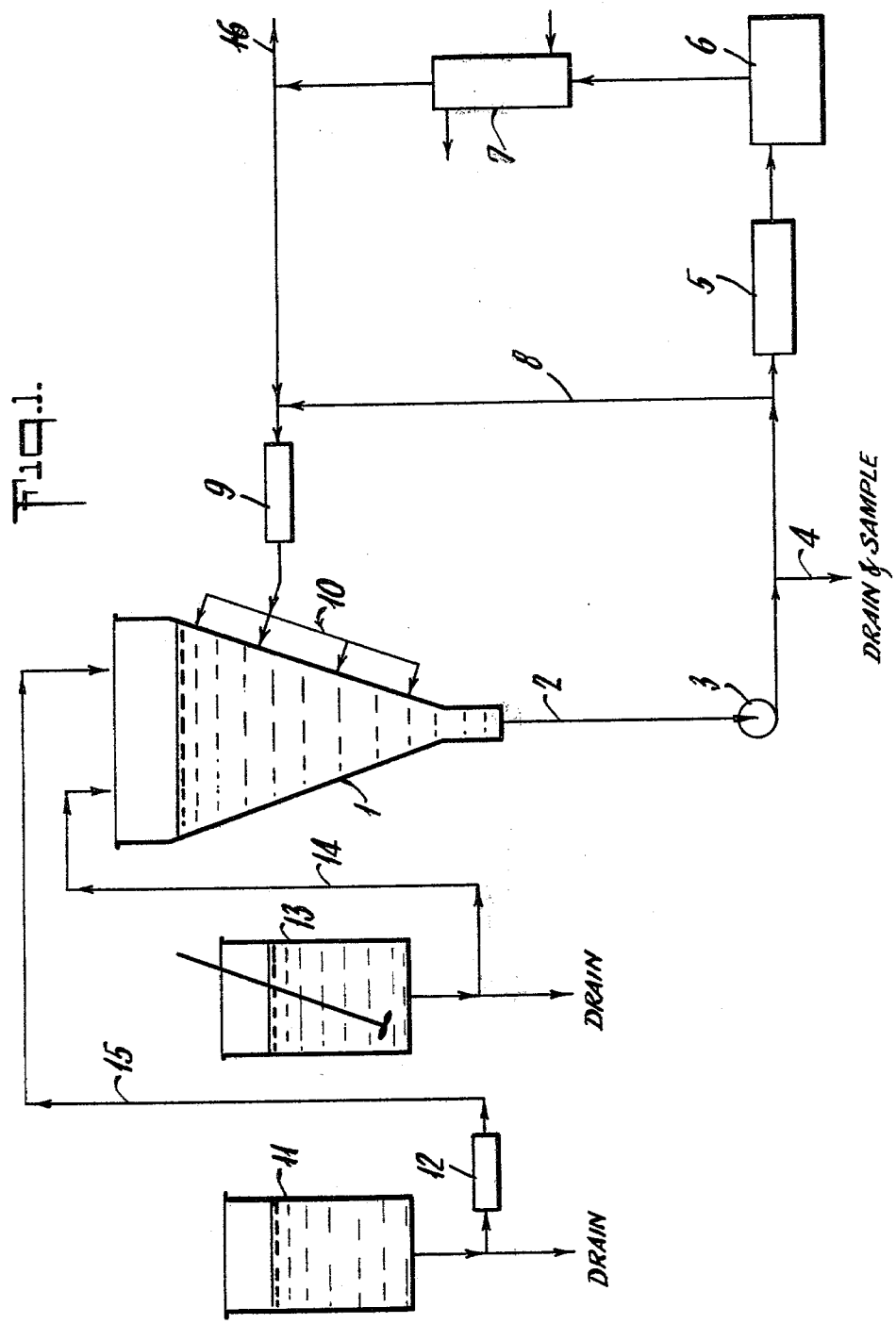
Figure 2:
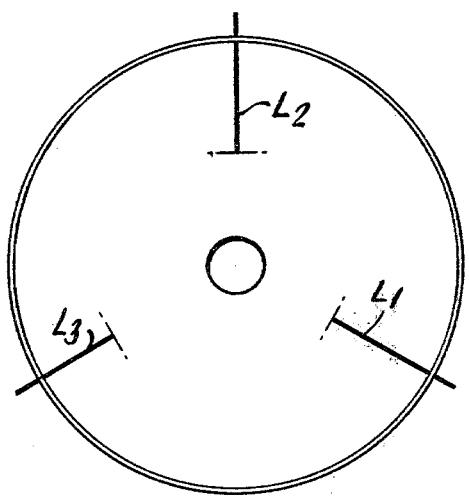
Figure 3:
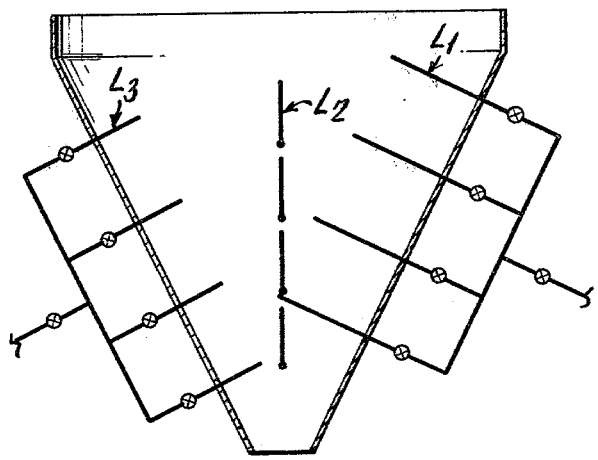

The organization and method of operation of the invention itself will best be understood from the following description when read in connection with the accompanying drawings wherein:

FIG. 1 is a diagrammatic view of the process;
FIG. 2 is a top plan view of Vessel 1; and
FIG. 3 is a diagrammatic cross-section through Vessel 1.

In FIG. 1, the holding tank 1, equipped with temperature control means (not shown), is positioned in communication with feed pump 3 via line 2, static mixer 5, homogenizer 6, static mixer 9 and entry ports 10. Optional by-pass line 8 is in communication with feed pump 3 and static mixer 9 and is used to impart some sort of flow pattern to the stream before passing it through the homogenizer 6 or the heat exchanger 7. The optional drain valve 4 is shown in communication with feed pump 3 and static mixer 5 but may be located at any point in the piping network. Also, not shown are the valves and flow meters which are employed in connection with the required pumping means.

In FIG. 1, the holding tank 1 is a conical vessel which is equipped with control valves (not shown) to regulate the temperature so as to maintain the product at a desired temperature or to melt selected solids. A conical vessel is preferred, however, other suitable shapes may be employed. An optional jacket may also be employed around the vessel to help regulate the temperature. Circulation is directed through a piping network via line 2 which can recycle the material, direct it through mixers 5 and 9 and or homogenizer 6, regulate the temperature using an in-line heat exchanger 7 and finally direct the material to the holding vessel 1. The circulation loops are so arranged that it is possible to have all or part of the stream (0-100%) pass through a static mixer 9 and return to the holding tank while the other portion passes through a second static mixer 5 which is in series with an in-line homogenizer 6 and a heat exchanger 7. Before returning it to the holding vessel 1, the second portion is recombined with the first portion and is further mixed in static mixer 9. The entry of the combined streams into the holding tank is accomplished by means of entry ports which are capable of distributing flow of the liquids or dispersed product at any desired levels and at adjustable flow rates. In FIG. 2, a top view of the main vessel is depicted showing the position of entry. For convenience, only three entry ports are shown in the drawing, however, any number of entry ports may be employed depending upon the size of the holding vessel. In FIG. 3, a side view of the main vessel is depicted showing the position of the various entry ports.

Circulation of the mixture is continued until the desired level of homogeneity is achieved. Samples of the material can be taken via a drain valve 4 which, for convenience is positioned between feed pump 3 and static mixer 5, but can be positioned at any convenient position along the piping network. Depending upon the congealing point of the dispersion, the temperature of the streams should be maintained within a range of about 1° to 30° C. above the congealing point. The preferred temperature is about 5° C. above the congealing point. The range can be increased or decreased, however, depending upon the size of the heat exchanger. After the desired level of homogeneity has been reached, the product is directed to the packaging equipment via line 16 (equipment not shown).

Optimal mixing of the dispersion is achieved through the use of multiple entry ports which are located approximately 120° from each other (FIG. 2). It is preferred to use entry ports which have varying lengths and to use a staggered arrangement of the heights of the entry ports. The use of nozzles (not shown) on the entry ports and baffles (not shown) in the holding tank is also desirable.

The solids melt tank 11 and the slurry tank 13 illustrated in FIG. 1 are both optional features in the piping network. The solids melt tank 11 is only required for certain types of products which are solids at ambient temperatures and will melt when heat is applied to them, such as certain hydrocarbon bases; esterified waxes and alcohols; oils; solid surfactants; stearates; monohydroxy and polyhydroxy alcohols, such as paraffin; beeswax; stearic acid; cetyl alcohol; and glyceryl monostearate. In addition, some oil soluble materials will not be readily soluble in the oil phase upon the formation of the emulsion; therefore, it is preferred to use a melt tank to prepare such solutions. When a melt tank is employed, it is preferred to use an in-line filter in conjunction with the melt tank. The slurry tank, which is equipped with an agitator, is only required if solids are to be suspended in a separate liquid phase. When the optional tanks are employed, the stream is feed into the holding tank via lines 14 and 15.

The creams or cream bases which can be prepared in accordance with the process of the invention are semisolid dispersions of either the oil-in-water or the water-in-oil type. The creams can include from about 10 to about 90% by weight of an oil phase and from about 90 to about 10% by weight of an aqueous phase. The oil phase generally comprises from about 70 to about 90% by weight of an oil material such as petrolatum, pegoxyl 7 stearate or heavy mineral oil, etc. Other ingredients which can be present in the oil phase include emulsifiers, emollients such as sorbitan monooleate, propylene glycol, a wax such as spermaceti, perfumes, and/or oil soluble pharmaceutical materials, for example. If some of the ingredients are not soluble in either phase, they can be suspended in the finished emulsion.

The aqueous phase generally includes about 70 to about 90% by weight of water and from about 10 to about 30% by weight of emulsifiers, emollients and/or preservatives. Other ingredients which can be present in the aqueous phase include antifoam agents, pharmaceutical materials, perfumes and dyes, for example.

An emulsifier can be included in the aqueous phase and/or the oil phase separately or mixed with the two phases. Emulsifiers suitable for use in the present process include those of the anionic, cationic and nonionic types, all of which are well known to those skilled in the art.

Other ingredients which can be included in either or both phases separately or mixed with the two phases include film-forming agents, astringents, deodorants, dyes, perfume, opacifiers, antifoam agents and solvents.

The advantages of the present invention over the prior art inventions include the elimination of extraneous tanks and agitation systems, elimination of transfer time required for mixing the oil and water phases, increased process control and greater process latitude. The latter two advantages are obtainable through subdivision of a complex manufacturing process into a series of unit operations which can be easily defined and controlled. The process described above is essentially a semicontinuous process, however, the process can be made continuous by adding to the main vessel an amount of the mixture of aqueous and oil phases equal to the amount of product withdrawn.

The following examples illustrate how the invention is carried into effect but is not meant to be limiting on the invention since it will be obvious to those skilled in the art how various changes can be made.

EXAMPLE 1

|  | % (w/w) |
|---|---|
| Aqueous Phase | |
| Purified Water | 73.8 |
| Benzoic Acid | 0.2 |
| Oil Phase | |
| Pegoxyl 7 Stearate | 20.0 |
| Peglicol 5 Oleate | 3.0 |
| Heavy Mineral Oil | 3.0 |

Procedure

The pegoxyl 7 stearate, peglicol 5 oleate and heavy mineral oil are mixed while being melted and heated to 140° F. Hot purified water (120° F.) is transferred to the main vessel and circulated through the homogenizer. The benzoic acid is added to the water and the mixture is circulated until the benzoic acid is completely dissolved. The temperature of the solution stays at 120° F. The oil phase is added to the water phase and the temperature in the main vessel upon completion of the addition rises to 123° F. The two phases are circulated through the homogenizer until an emulsion is formed. The emulsion is withdrawn from the circulation system through a heat exchanger at a temperature of 90° F. Samples of the product are taken periodically from the batch as it passes through the heat exchanger.

EXAMPLE 2

| Lubricating Jelly Ingredients | % (w/w) |
|---|---|
| CMC Type 7HF | 1.85 |
| Kelgin LV | 1.08 |
| Methylparaben | 0.15 |
| Propylene Glycol | 3.75 |
| Glycerin | 11.25 |
| Potassium Hydroxide | 0.03 |
| Boric Acid | 3.00 |
| Water | 78.89 |

Procedure

The water (at 75° C.) and the boric acid are added into the main vessel. The mixture is circulated through the bypass loop until a solution is formed. To this solution, Kelgin LV is added and the mixture is circulated again until the Kelgin is completely dissolved.

In the slurry tank, a slurry of propylene glycol, glycerin, CMC and methylparaben is prepared. While the mixture is circulated through the homogenizer, the slurry is transferred to the main vessel and the circulation is maintained until a solution is formed. During this circulation period, the temperature of the jelly is maintained at 70° to 75° C. until all the solids are in solution.

This solution, with the aid of the heat exchanger, is cooled to 30° to 35° C. to form the lubricating jelly.

EXAMPLE 3

|  | % (w/w) |
|---|---|
| Aqueous Phase | |
| Purified Water | 73.8 |
| Benzoic Acid | 0.2 |
| Oil Phase | |
| Pegoxyl 7 Stearate | 20.0 |
| Peglicol 5 Oleate | 3.0 |
| Heavy Mineral Oil | 3.0 |

Procedure

The pegoxyl 7 stearate, peglicol 5 oleate and heavy mineral oil are mixed while being melted and heated to 180° F. Hot purified water (180° F.) is transferred to the main vessel and circulated through the homogenizer. The benzoic acid is added to the water and the mixture is circulated until the benzoic acid is completely dissolved. The temperature of the solution drops to 165° F. The oil phase is added to the water phase and the temperature in the main vessel upon completion of the addition rises to 167° F. The two phases are circulated through the homogenizer until an emulsion is formed. The emulsion is withdrawn from the circulation system through a heat exchanger at a temperature of 110° F. Samples of the product are taken periodically from the batch as it passes through the heat exchanger.

EXAMPLE 4

| A. | % (w/w) |
|---|---|
| Oil Phase | |
| Mineral Oil | 25.0 |
| Microcrystalline Wax | 10.0 |
| Cetyl Alcohol | 5.0 |
| Mixed Lanolin Alcohols | 10.0 |
| Sorbitan Sesquioleate | 3.0 |

| -continued | |
|---|---|
| A. | % (w/w) |
| Aqueous Phase | |
| Glycerin | 3.0 |
| Methylparaben | 0.2 |
| Purified Water | 43.8 |

Procedure

The oil phase components are added to the melt tank and the mixture is heated to 70° C. The molten oil phase is then transferred to the main vessel. The aqueous phase ingredients are added to the main vessel while circulating the contents through the homogenizer until a dispersion is formed. The dispersion is cooled to 30° C. with the aid of the heat exchanger to form an ointment.

B. The process described above can be made continuous by adding to the main vessel an amount of the mixture of oil and aqueous phases equal to the amount of product drawn off after it passes through the heat exchanger.

We claim:

1. A process for preparing a semisolid dispersion which comprises circulating a mixture of an oil phase and an aqueous phase from a main vessel through one or more mixing devices and one or more homogenizers in series until a semisolid dispersion is formed and withdrawing the dispersion from the system through a heat exchanger.

2. The process of claim 1 wherein the aqueous phase is first circulated through the mixers and homogenizers at an elevated temperature, followed by addition of the oil phase to the aqueous phase, after which the mixture of the two phases is circulated through the mixers and homogenizers at elevated temperatures until a dispersion is formed after which the dispersion is withdrawn from circulation through a heat exchanger.

3. The process of claim 2 wherein the temperature of the water phase and the oil and water phase is about 5° F. above the congealing point.

4. A process for the continuous preparation of a semisolid dispersion which comprises circulating a mixture of an oil phase and aqueous phase from a main vessel through one or more mixing devices and one or more homogenizers in series until a semisolid dispersion is formed, withdrawing a portion of said dispersion from the system at intervals through a heat exchanger while adding an amount of the mixture of the oil and aqueous phases equal to the amount withdrawn.

* * * * *